(12) United States Patent
Gokhale et al.

(10) Patent No.: US 8,328,775 B2
(45) Date of Patent: Dec. 11, 2012

(54) METERED DROP BOTTLE FOR DISPENSING MICROLITER AMOUNTS OF A LIQUID IN THE FORM OF A DROP

(75) Inventors: Satish Madhukar Gokhale, Pune (IN); Abhijit Takale, Pune (IN); Prashant Kane, Baroda (IN)

(73) Assignee: Sun Pharma Advanced Research Company Limited, Mumbai (IN)

( * ) Notice: Subject to any disclaimer, the term of this patent is extended or adjusted under 35 U.S.C. 154(b) by 568 days.

(21) Appl. No.: 12/518,149

(22) PCT Filed: Dec. 7, 2007

(86) PCT No.: PCT/IN2007/000576
§ 371 (c)(1),
(2), (4) Date: Oct. 8, 2009

(87) PCT Pub. No.: WO2008/068775
PCT Pub. Date: Jun. 12, 2008

(65) Prior Publication Data
US 2010/0016814 A1    Jan. 21, 2010

(30) Foreign Application Priority Data
Dec. 7, 2006  (IN) .......................... 2009/MUM/2006

(51) Int. Cl.
*A61M 35/00* (2006.01)
*B65D 47/18* (2006.01)
(52) U.S. Cl. ....................................... 604/298; 222/420

(58) Field of Classification Search .......... 604/294–302; 222/420, 632
See application file for complete search history.

(56) References Cited

U.S. PATENT DOCUMENTS

| | | | | |
|---|---|---|---|---|
| 2,688,424 A | * | 9/1954 | Keiter | 222/215 |
| 3,016,898 A | * | 1/1962 | Erwin | 604/298 |
| 3,325,031 A | * | 6/1967 | Singier | 215/247 |
| 3,405,843 A | * | 10/1968 | Watson, Jr. | 222/95 |
| 3,741,439 A | * | 6/1973 | Vehrs | 222/103 |
| 3,926,347 A | * | 12/1975 | Low et al. | 222/181.2 |
| 3,934,585 A | * | 1/1976 | Maurice | 604/298 |
| 4,111,200 A | * | 9/1978 | Sbarra et al. | 604/298 |
| 4,177,939 A | * | 12/1979 | Thomas | 222/153.13 |

(Continued)

FOREIGN PATENT DOCUMENTS
EP    1486192 A1    12/2004

OTHER PUBLICATIONS

International Search Report of PCT/IN2007/000576, date of mailing Jun. 10, 2008.

*Primary Examiner* — Melanie Hand
*Assistant Examiner* — Paula Craig
(74) *Attorney, Agent, or Firm* — Westerman, Hattori, Daniels & Adrian, LLP

(57) ABSTRACT

The present invention relates to a metered drop bottle for dispensing microliter amounts of a liquid in the form of a drop comprising: (a) a bottle with a flexible portion on the walls to decrease the internal volume by a fixed volume; (b) a plunger with a fixed stroke for depressing the flexible portion of the walls of the bottle; and (c) a nozzle tip having an internal and/or outer diameter no more than 1.2 mm.

15 Claims, 12 Drawing Sheets

U.S. PATENT DOCUMENTS

| | | | | |
|---|---|---|---|---|
| 4,543,096 | A * | 9/1985 | Keene | 604/300 |
| 4,629,456 | A * | 12/1986 | Edwards | 604/300 |
| 4,634,023 | A | 1/1987 | Tanaka et al. | |
| 4,771,769 | A * | 9/1988 | Hegemann et al. | 128/200.22 |
| 4,787,536 | A * | 11/1988 | Widerstrom | 222/212 |
| 4,792,334 | A * | 12/1988 | Py | 604/301 |
| 4,809,914 | A * | 3/1989 | Goncalves | 239/327 |
| 5,024,355 | A * | 6/1991 | Jouillat et al. | 222/162 |
| 5,085,651 | A * | 2/1992 | Py | 604/298 |
| 5,261,571 | A * | 11/1993 | Goncalves | 222/214 |
| 5,356,052 | A * | 10/1994 | Poynter | 222/420 |
| 5,390,822 | A * | 2/1995 | Lataix | 222/30 |
| 5,401,259 | A * | 3/1995 | Py | 604/294 |
| 5,487,489 | A * | 1/1996 | Weiss et al. | 222/1 |
| 5,578,020 | A * | 11/1996 | Mosley | 604/295 |
| 5,582,330 | A * | 12/1996 | Iba | 222/212 |
| 5,613,957 | A * | 3/1997 | Py | 604/294 |
| 5,624,057 | A * | 4/1997 | Lifshey | 222/212 |
| 5,673,822 | A * | 10/1997 | Chalmin et al. | 222/183 |
| 6,105,828 | A * | 8/2000 | Kanner et al. | 222/212 |
| 6,129,248 | A * | 10/2000 | Hagele | 222/420 |
| RE37,047 | E * | 2/2001 | Py | 604/294 |
| 6,197,008 | B1 * | 3/2001 | Hagele | 604/295 |
| 6,814,265 | B2 * | 11/2004 | Clifford et al. | 222/420 |
| 6,875,201 | B1 * | 4/2005 | Kawashima et al. | 604/295 |
| 7,438,704 | B1 * | 10/2008 | Kawashima et al. | 604/295 |
| 7,846,140 | B2 * | 12/2010 | Hagele | 604/295 |
| 2002/0084290 | A1 * | 7/2002 | Materna | 222/420 |
| 2004/0140319 | A1 * | 7/2004 | Gerondale | 222/1 |
| 2005/0133543 | A1 * | 6/2005 | Clifford et al. | 222/420 |
| 2005/0159715 | A1 | 7/2005 | Kusu | |
| 2005/0165368 | A1 * | 7/2005 | Py et al. | 604/289 |
| 2005/0274744 | A1 | 12/2005 | Spada et al. | |
| 2006/0108378 | A1 * | 5/2006 | Cohen et al. | 222/211 |
| 2007/0233020 | A1 * | 10/2007 | Hearne | 604/295 |
| 2007/0233021 | A1 * | 10/2007 | Poisson et al. | 604/295 |
| 2009/0082739 | A1 * | 3/2009 | Cress | 604/298 |

* cited by examiner

METERED DROP BOTTLE FOR DISPENSING MICROLITER AMOUNTS OF A LIQUID IN THE FORM OF A DROP

This application is a national stage application of PCT/IN07/00576, filed Dec. 7, 2007, and claims priority to Indian Application No. 2009/MUM/2006 filed Dec. 7, 2006.

FIELD OF THE INVENTION

The present invention relates to a metered drop bottle for dispensing microliter amounts of a liquid in the form of a drop.

BACKGROUND OF THE INVENTION

Liquid drop dispensers of the type to which the present invention pertains are available in various sizes and shapes and act by various mechanisms for dispensing of the liquid contents. One problem associated with conventional dispensers was the difficulty in accurately controlling the amount of medicine dispensed, i.e., the number of drops and the volume of the drop to be dispensed. There is a need for dispensing microliter amounts of a liquid in the form of a drop, especially during the administration of medicaments to a body cavity. This is because if the drop volume is not controlled, excess medicament administered may lead to the risk of systemic toxicity by the medicament and also cause a waste of medicaments. This is particularly relevant for ocular medicaments wherein the systemic toxicity is, in part, a function of the relatively large size of the commercial eyedrops.

The average size of a conventional ophthalmic eyedrop is approximately 50 to 70 microliter. However, the tear film normally contains only 7 to 10 microliter. If an eyedrop is instilled, the tear film can momentarily hold as much as 30 microliter before the subject blinks. The remainder of the eyedrop, at least 20 to 40 microliter, spills out onto the cheek. Rapid blinking quickly restores the normal tear volume by pumping the excess into the nasolacrimal system. It is estimated that 80% of an eyedrop drains via this route, where it can be systemically absorbed. With larger eyedrops, more medicament passes into the nasolacrimal sac, increasing absorption and the risk of toxicity (Brown, R H et al., Am J Ophthal., 99, April 1985, 460-464). From a biopharmaceutical and toxicological point of view, it has been suggested that the decrease in drop size to between 5 to 15 microliter would reduce the rate of medicament loss through drainage, the incidence of systemic toxic effects, and, in addition, the cost of therapy (Sklubalova Z et al., DDIP, 32, 2006, 197-205). Brown, R H et al tested a bottle having a delivery orifice tip. They varied the internal and outer diameter of the tip and found that for fixed internal diameters in the range from about 0.02 inches to about 0.06 inches, increase in outer diameter from about 0.02 inches to about 0.18 inches resulted in an increase in drop size from about 10 microliter to about 60 microliter. An eyedrop of less than 25 microliter was always delivered when the outer diameter of the tip was less than 0.047 inches. Brown, R H et al further discloses that the bottle has two chambers, an inner chamber containing the liquid and an outer chamber that ends in the delivery orifice tip on one end and a second narrow aperture on the other end separating the outer chamber from the inner chamber. When the bottle is squeezed, the liquid emerges as a drop rather than a stream.

U.S. Pat. No. 5,356,052 relates to drop dispenser for accurate dispensing of drops of a predetermined size. The dispenser has a neck that has a flat flow passage or an orifice leading to a chamber, the chamber ending in a delivery aperture. The liquid from the container is forced into a flat flow passage in the neck and discharged into a chamber in the tip where the liquid coalesces. The liquid is then dispensed through an aperture whose dimensions determine the size of the drop dispensed.

U.S. Pat. No. 5,673,822 relates to a device for the dropwise delivery of a fluid contained in a flexible vial, the device comprising a tubular casing capable of surrounding the vial, wherein the casing is provided with a bottom portion whose inner surface lies opposite the outer surface of the bottom wall of the vial, and the bottom portion of the casing is equipped with a resiliently displaceable tab which can be moved so as to press against the bottom wall of the vial in order to squeeze the vial and drive out a drop of fluid. It is disclosed that the stroke of the tab is ideally determined such that only one drop is expelled. In order to enable that the vial be squeezed, the whole bottle is made flexible. As the bottle itself should maintain its rigidity, this flexibility is limited. The tab presses on a flat wall and we find that generally volume displaced may be large because a full wall on the bottle rather than a fixed portion of the wall is depressed.

SUMMARY OF THE INVENTION

In one aspect of the invention, there is provided a metered drop bottle for dispensing microliter amounts of a liquid in the form of a drop comprising:
 (a) a bottle with a flexible portion on the walls to decrease the internal volume by a fixed volume;
 (b) a plunger with a fixed stroke for depressing the flexible portion of the walls of the bottle;
 (c) a nozzle tip having an internal and/or outer diameter no more than 1.2 mm.

BRIEF DESCRIPTION OF THE DRAWINGS

Many aspects of the invention can be better understood with reference to the following drawings.

The components in the drawings are not necessarily to scale, emphasis instead being placed upon clearly illustrating the principles of the present invention. Moreover, in the drawings, like reference numerals designate corresponding parts throughout the several views.

Embodiment 1: A metered drop bottle with a flexible notch area; an external cover surrounding the bottle, wherein the plunger is in-built in the side walls of the cover; and a nozzle.

Figure 1:
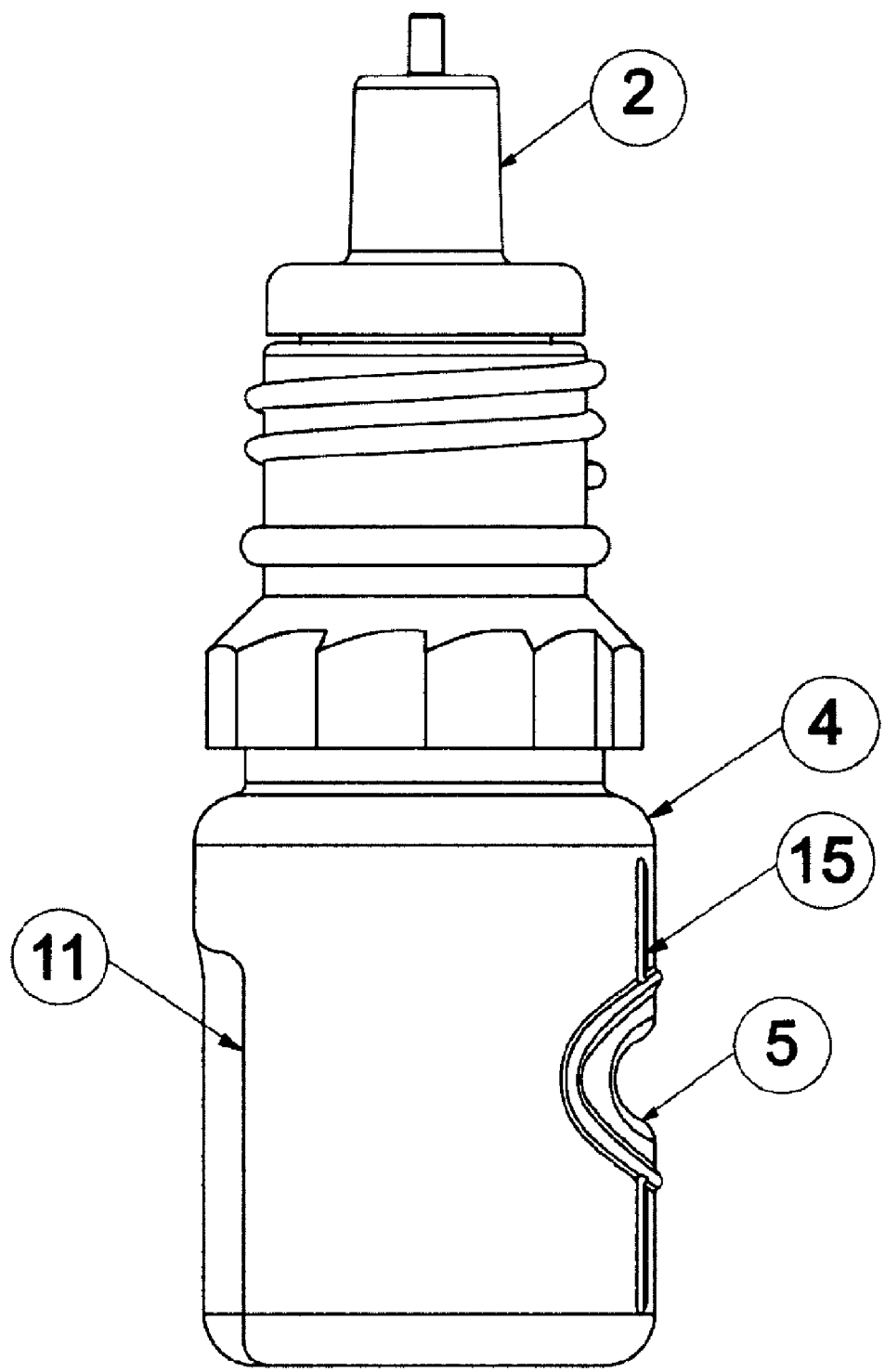

FIG. 1: Metered drop bottle fitted with nozzle—external view

Figure 2:
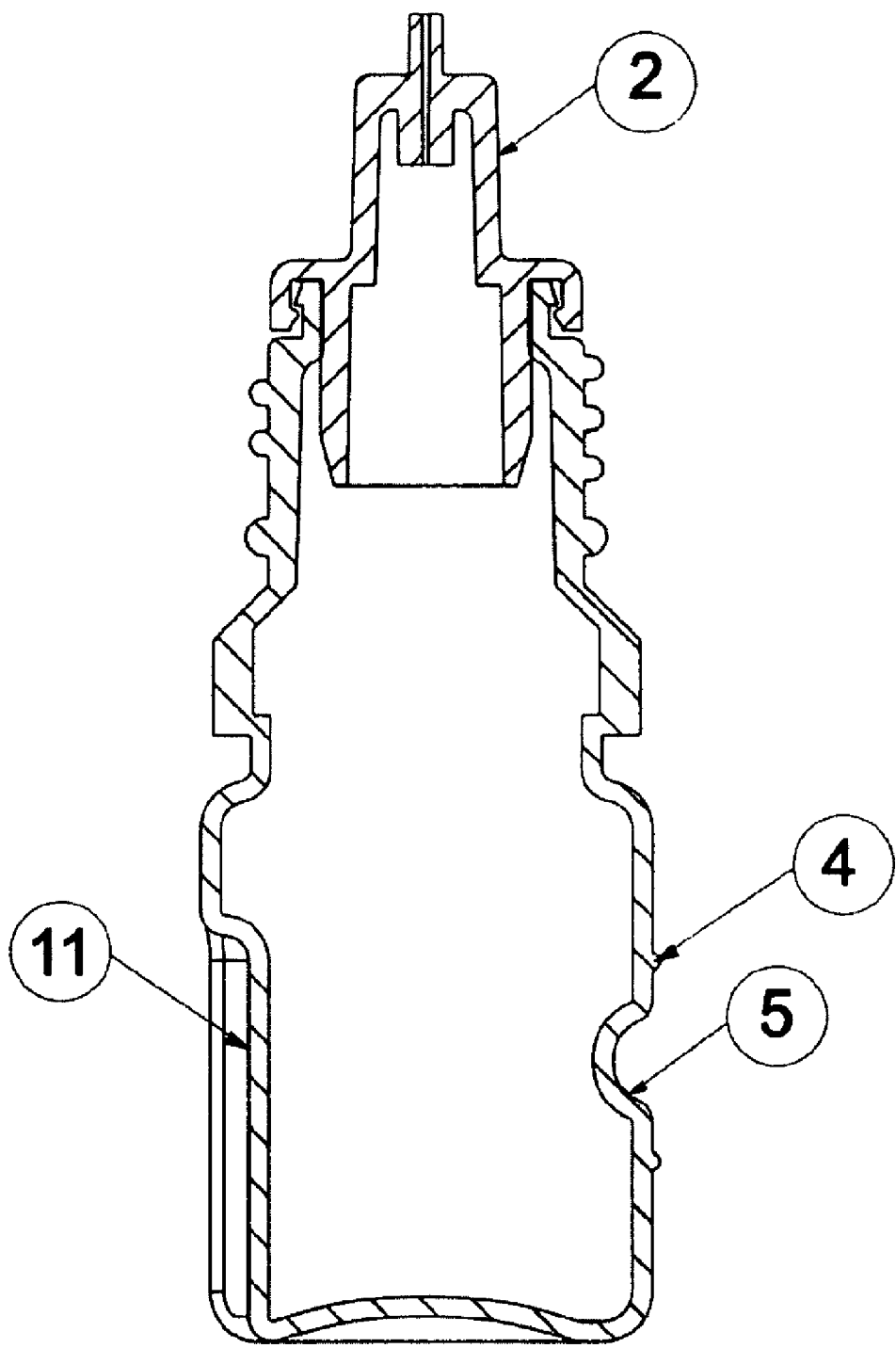

FIG. 2: Metered drop bottle fitted with nozzle—cross section view

Figure 3:
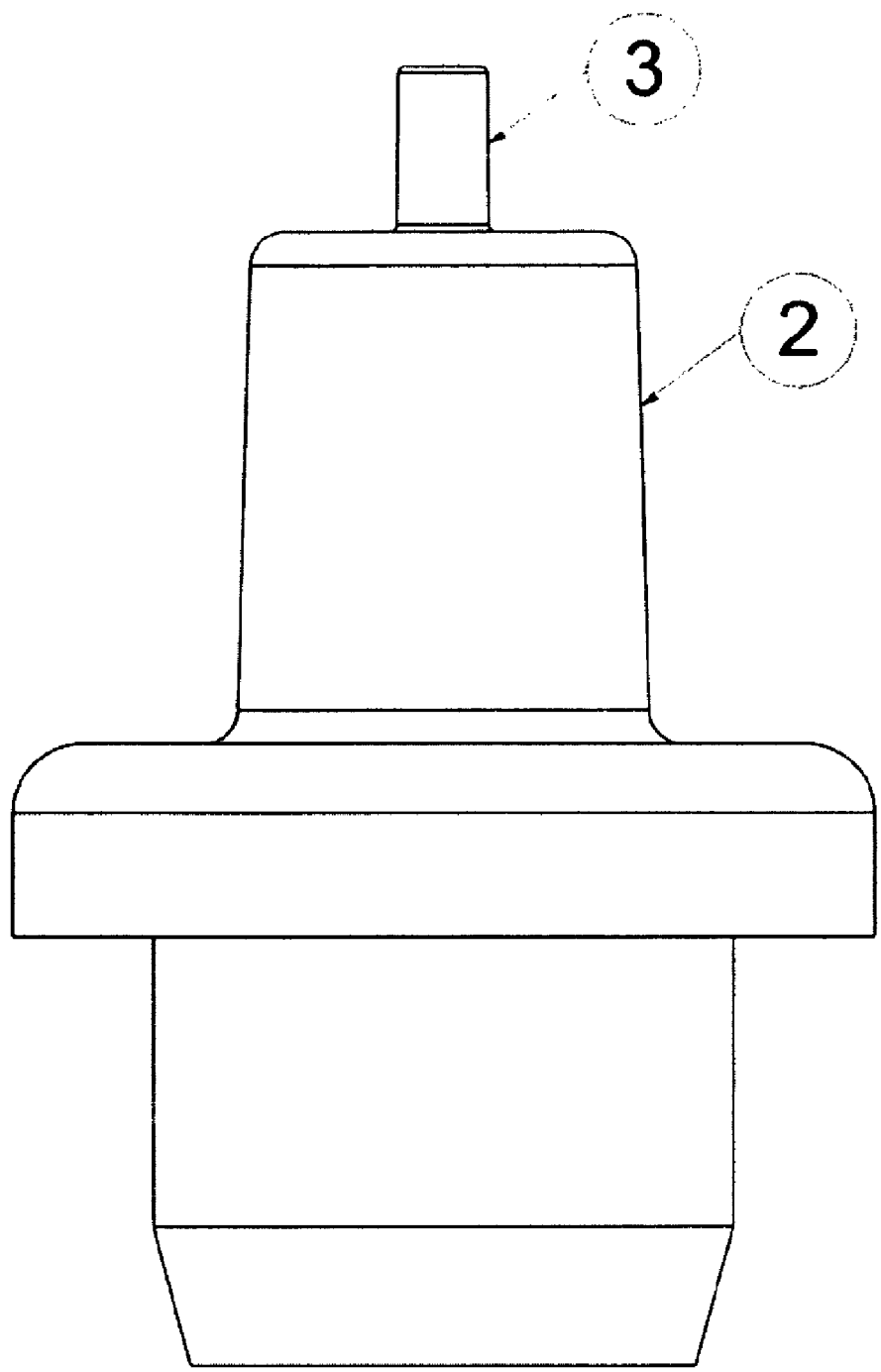

FIG. 3: Nozzle—external view

Figure 4:
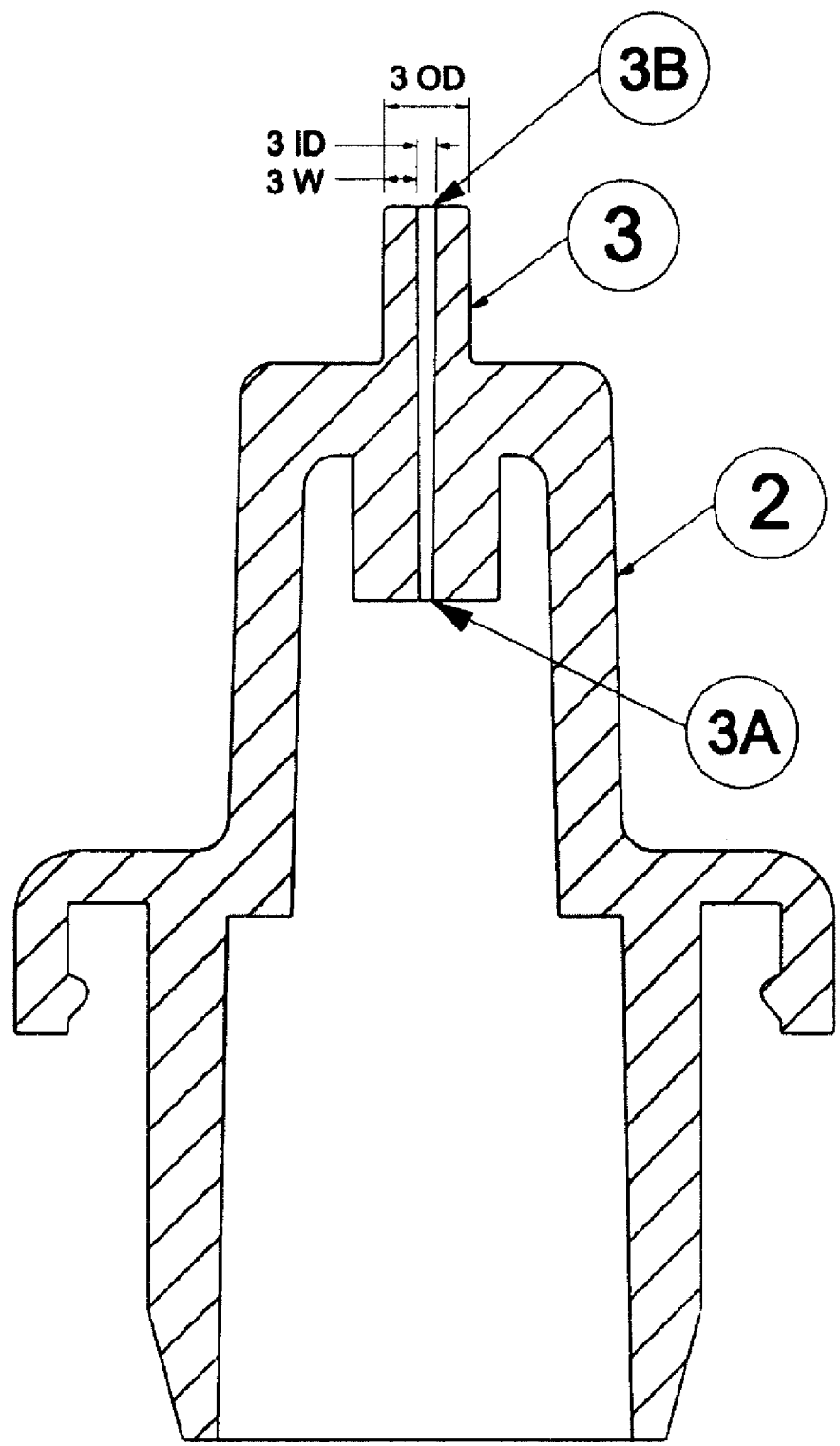

FIG. 4: Nozzle of an embodiment—cross section view

Figure 5:
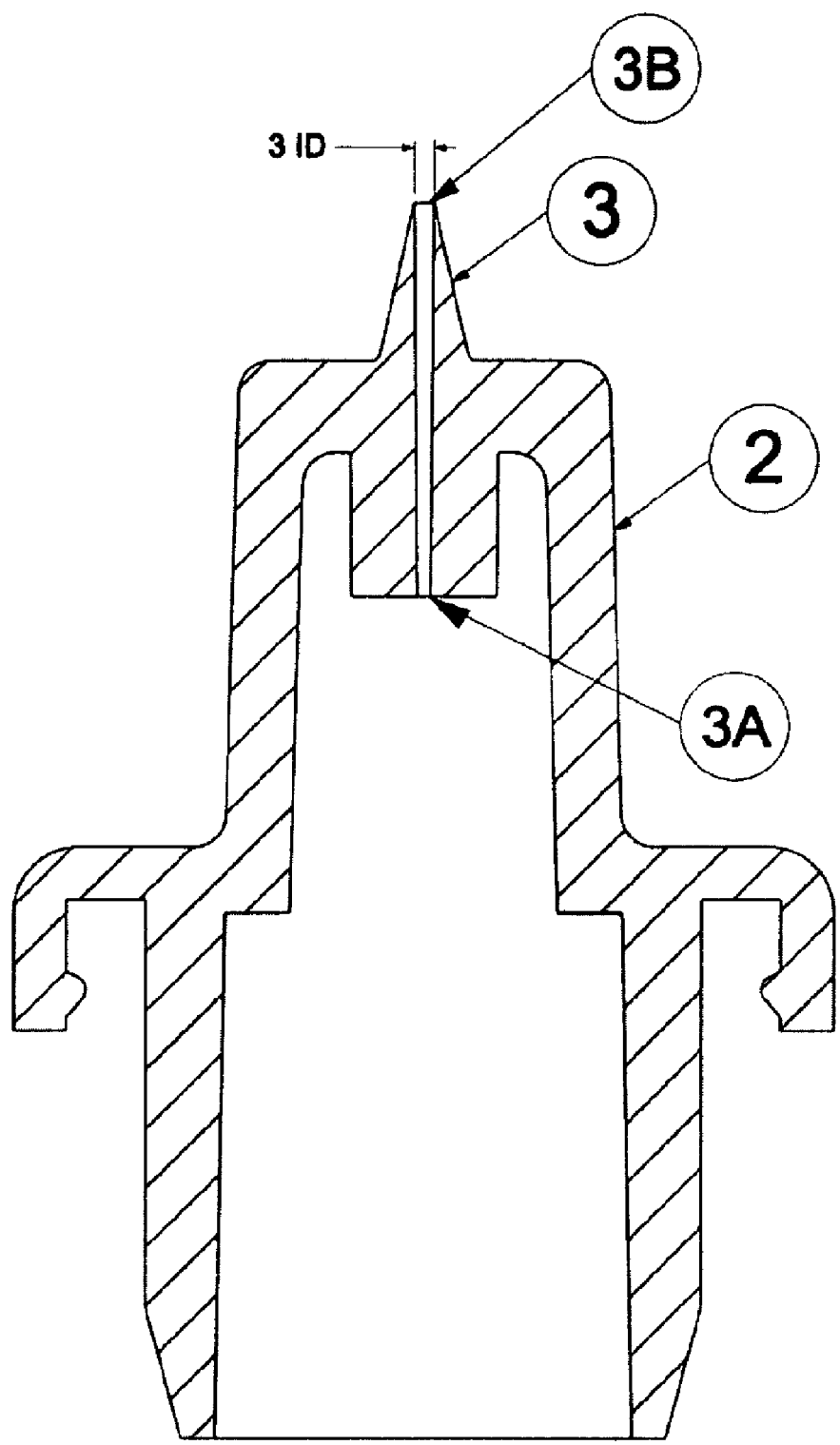

FIG. 5: Nozzle of another embodiment—cross section view

Figure 6:
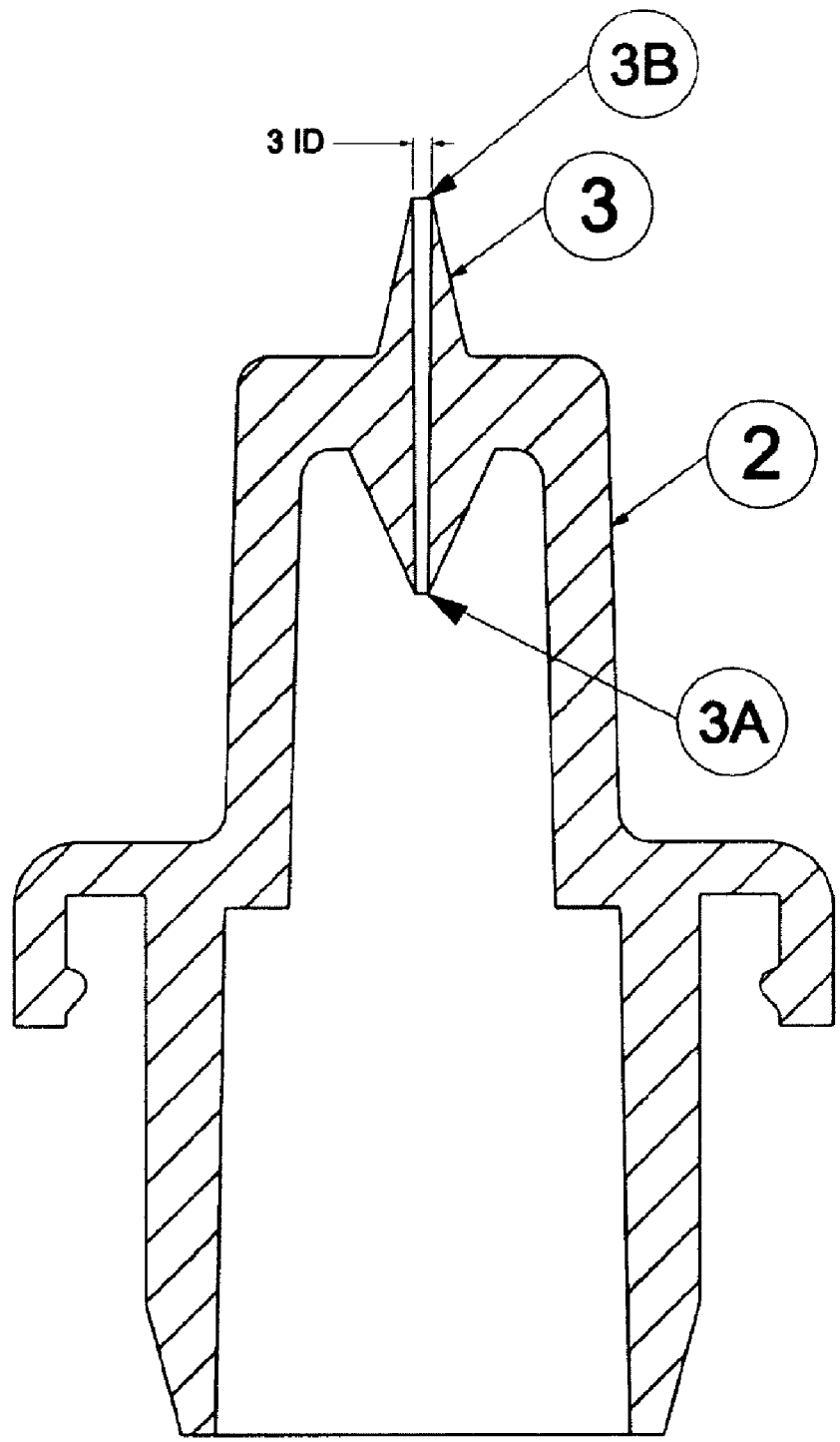

FIG. 6: Nozzle of yet another embodiment—cross section view

Figure 7:
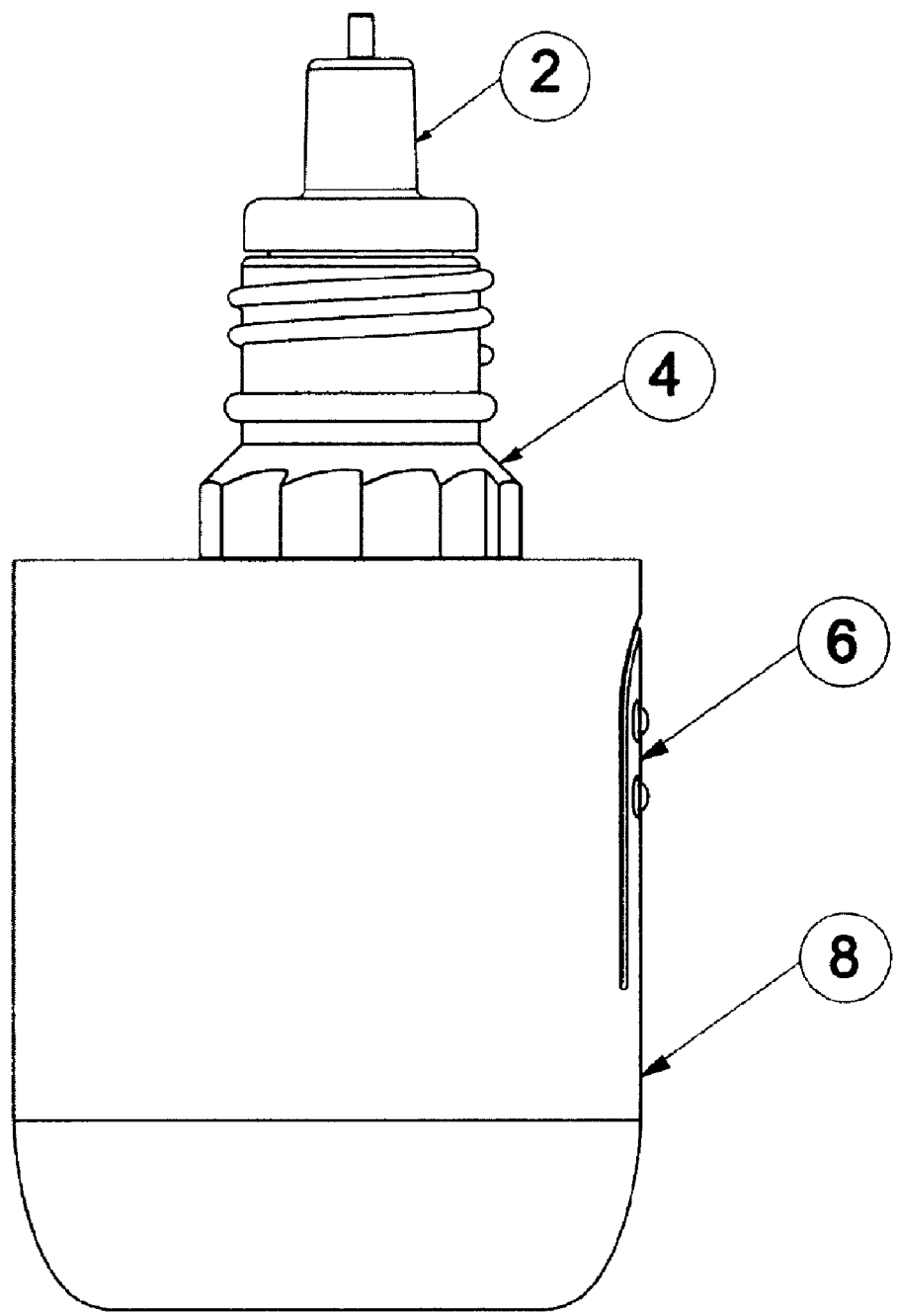

FIG. 7: Metered drop bottle fitted with nozzle and an external cover containing the plunger—external view FIG. 8: Metered drop bottle fitted with nozzle and an external cover containing the plunger—cross section FIG. 9: Metered drop bottle fitted with nozzle, an external cover containing the plunger, dispensing aid and cap—Front external view of the exploded assembly FIG. 10: Metered drop bottle fitted with nozzle, an external cover containing the plunger, dispensing aid and cap—Isometric external view of the exploded assembly FIG. 11: Metered drop bottle fitted with nozzle, an external cover containing the plunger, dispensing aid and cap—Side cross section view of the exploded assembly Embodiment 2: A metered drop bottle with a flexible notch area; an external cover surrounding the bottle; a plunger which is separate from the external cover and fitted into the external cover before use and a nozzle.

Figure 11:
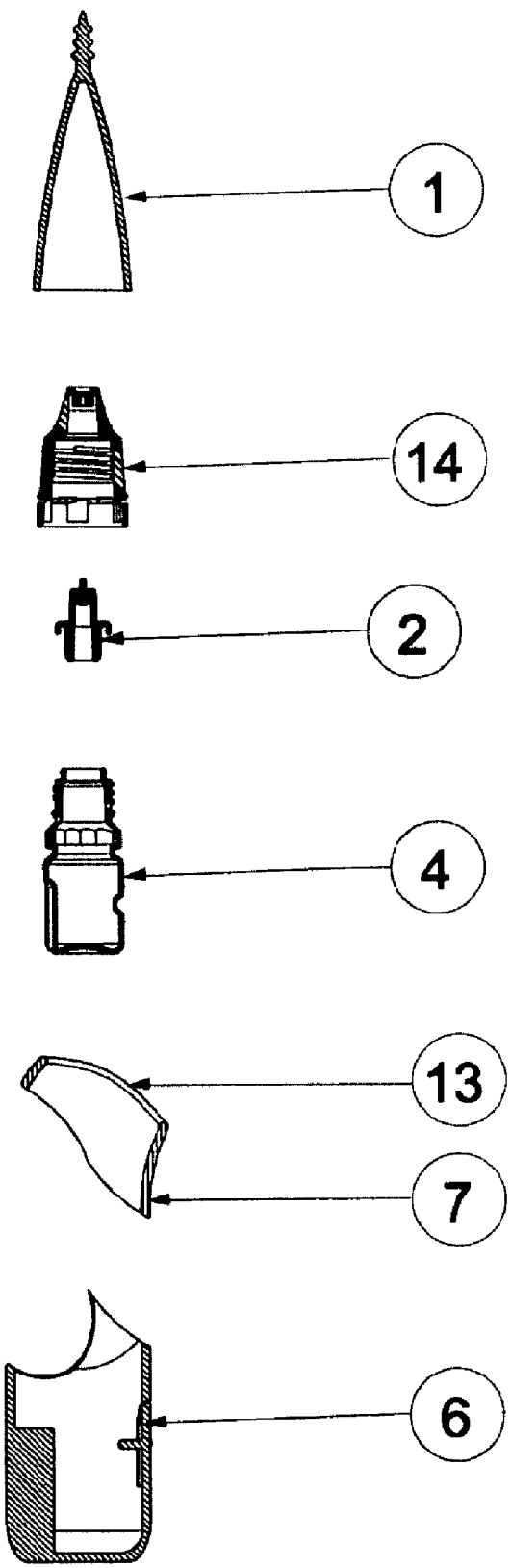
Figure 12:
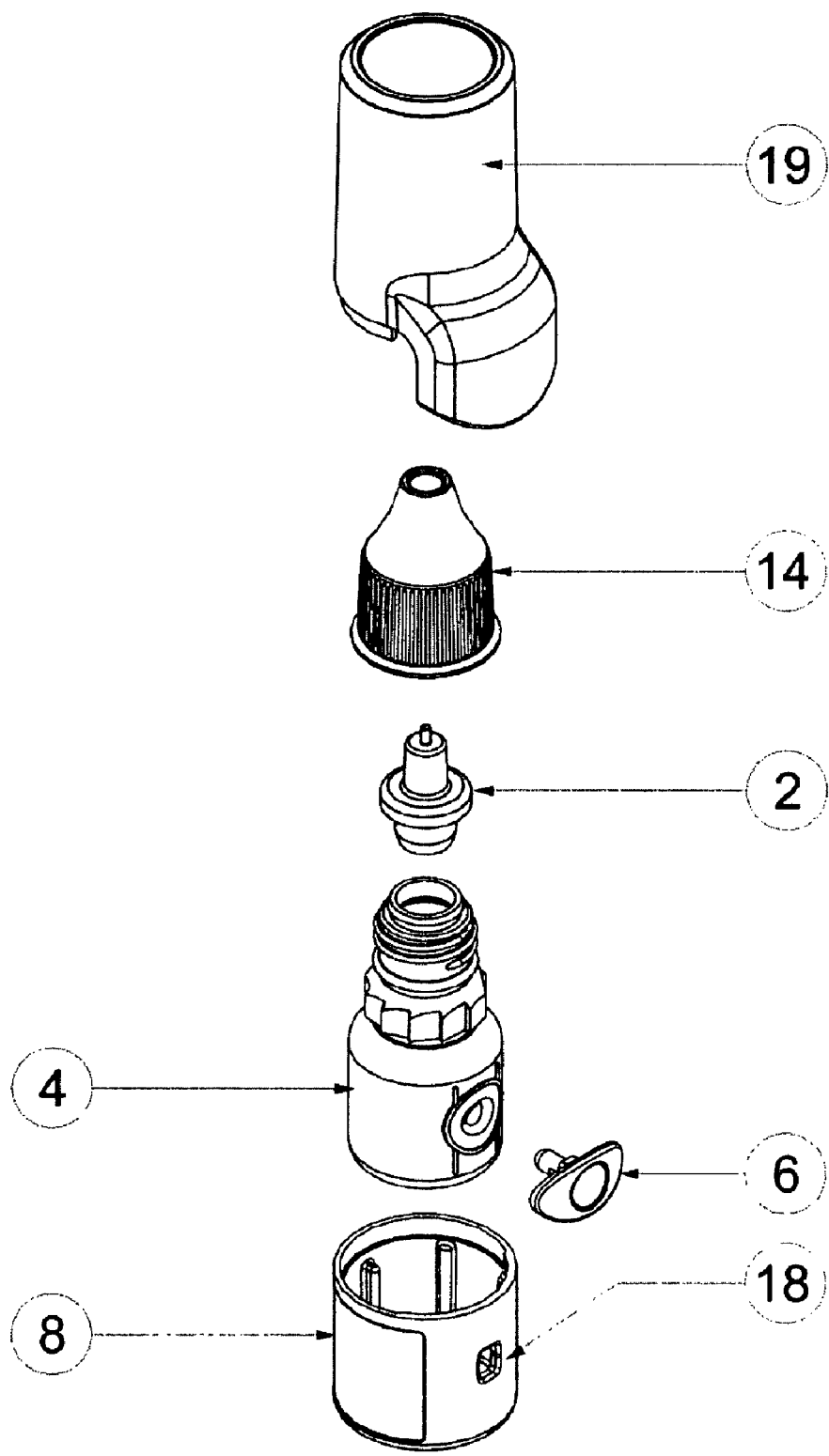

FIG. 12: Metered drop bottle with an external cover surrounding the bottle; a plunger which is separate from the external cover and fitted into the external cover before use and a nozzle—Front external view of the exploded assembly The figures only represent embodiments of the present invention. The embodiments are meant only for the purpose of illustration of the present invention. Different parts of the device of these embodiments are labeled in FIGS. 1 to 12 and the labeling is described in the schedule of the reference numerals herein below.

SCHEDULE OF REFERENCE NUMERALS

1: External Cap
2: Nozzle
3: Step in the nozzle (2)
3A: Aperture in the nozzle
3B: Nozzle tip
3 OD: Outer diameter of the nozzle tip
3 ID: Internal diameter of the nozzle tip
3 W: Platform width of the nozzle tip
4: Metered drop Bottle
5: Flexible notch area on the bottle (4)
6: Plunger
7: Eyedrop dispensing aid
8: External cover of the bottle (4)
9: Orientation indicator
11: Slot in the bottle (4)
13: Curvature of the top part of the eyedrop dispensing aid (7)
14: Bottle cap
15: Ribs around the flexible notch area of the bottle
16: Rib in external cover for mating with slot in the bottle (11)
18: Slot in the external cover for fitting the plunger (6)
19: Protective cap

DETAILED DESCRIPTION OF THE INVENTION

The device of the present invention is illustrated by embodiments described here in below.

The metered drop bottle of this invention can be used for administration of cosmetic or medicament liquids to the user. The metered drop bottle of the invention dispenses microliter amounts of a liquid in the form of a drop. The metered drop bottle of the invention dispenses a drop of predetermined size of about 14 microliter to about 25 microliter of the liquid to be dispensed. In a preferred embodiment, the metered drop bottle dispenses a drop of predetermined size of about 14 microliter to about 18 microliter of the liquid to be dispensed.

In a preferred embodiment of the present invention, the bottle of the invention is used for delivery of medicaments to the body cavities such as eyes, ears, nose and the like of the user. In a particularly preferred embodiment of the present invention, the bottle of the invention is used to administer medicament to the eyes of the patient. Typically the metered bottle is used to deliver ophthalmic medicaments to the user.

The present invention provides a metered drop bottle for dispensing microliter amounts of a liquid in the form of a drop comprising:

(a) a bottle with a flexible portion on the walls to decrease the internal volume by a fixed volume;
(b) a plunger with a fixed stroke for depressing the flexible portion of the walls of the bottle;
(c) a nozzle tip having an internal and/or outer diameter no more than 1.2 mm.

The metered drop bottle of the invention has a flexible portion on the walls and a plunger is provided for depressing the flexible portion of the bottle in order to decrease the internal volume of the bottle by a fixed volume. This fixed volume of the liquid from the bottle is displaced into the nozzle having a nozzle tip with an internal and/or outer diameter no more than 1.2 mm so as to dispense a drop of microliter amounts. We believe that this combination of the bottle of the invention with flexible portion on the walls, a plunger and the nozzle having a nozzle tip with an internal and/or outer diameter no more than 1.2 mm provides a drop of microliter amounts in a more consistent manner than the prior art bottles.

The metered drop bottle of the invention is generally made up of rigid materials but has a flexible portion on the walls. The flexible portion may be on the sidewalls or the bottom wall of the bottle. A plunger is provided for depressing the flexible portion of the bottle by an amount which would displace an equivalent volume of the liquid from the bottle to the nozzle. Generally the stroke length of the plunger and hence the amount of depression of the flexible wall of the bottle is so adjusted to displace an amount of liquid from the bottle to the nozzle which is about nearly the same amount as the microliter drop volume which is to be finally administered from the nozzle. This fixed amount of liquid displaced from the bottle to the nozzle makes possible dispensing of only one drop from the nozzle. If a larger amount of liquid were displaced from the bottle to the nozzle, a stream of the liquid would be dispensed from the nozzle instead of a single drop. In a preferred embodiment, the flexible portion on the walls of the bottle is a flexible notch area, which may be typically situated on the sidewalls of the bottle. The embodiment may further comprise ribs present around the flexible notch area in order to avoid excessive flexing of the bottle walls. The metered drop bottle of the invention may further comprise an external cover which surrounds the bottle and houses the plunger.

The nozzle of the metered drop bottle of the invention is designed such that, it, in combination with the flexible portion on the walls of the bottle and the plunger dispenses a single drop of microliter amounts of the liquid. It is preferred that the drop of the liquid dispensed has volume less than about 18 micro-liters. The nozzle tip of the bottle of the invention has an internal and/or outer diameter no more than 1.2 mm. The nozzle of the invention functions to produce and dispense microliter sized drop of the liquid to be dispensed. The nozzle tip at its dispensing end has an internal diameter and an outer diameter and the tip is connected to an aperture inside the nozzle by a capillary tapering from the dispensing tip to the aperture in the nozzle. The diameters of the aperture and the nozzle tip in conjugation with the surface tension of the liquid to be administered lead to the formation of a microliter sized drop. The diameters of the aperture and the nozzle tip can be varied to produce a fixed sized microliter volume. drop for liquids of different surface tensions. In an embodiment of the present invention the aperture has an internal diameter of about 0.2 mm and the nozzle tip has an internal diameter of about 0.6 mm and an outer diameter of about 1.2 mm. In another embodiment, both the internal and outer diameter of the nozzle tip are the same, and may range from about 0.6 mm to about 1.2 mm. The nozzle may be made from a hydrophobic material or it may be coated with a hydrophobic substance in order to reduce the wetting of the tip and avoid pooling of the liquid to form a larger drop.

In a preferred embodiment of the present invention, the bottle of the invention is used to administer medicament to the eyes of the patient. In this case, the bottle may have an eyedrop dispensing aid in order to avoid touching the nozzle of the bottle to the surface of the eye. An orientation indicator may also be provided to indicate to the patient whether the orientation of the bottle in relation to the eye is correct for proper dispensation of a desired sized drop into the eye.

In an embodiment of the invention, the metered drop bottle comprises a bottle with a flexible notch area; an external cover surrounding the bottle wherein with the plunger is in-built in the side walls of the cover; and a nozzle tip with an internal and/or outer diameter no more than 1.2 mm.

In another embodiment of the invention, the metered bottle comprises a bottle with a flexible notch area; an external cover surrounding the bottle; a plunger which is separate from the external cover and fitted into the external cover before use and a nozzle tip with an internal and/or outer diameter no more than 1.2 mm.

Embodiment 1: A metered drop bottle with a flexible notch area; an external cover surrounding the bottle, wherein the plunger is in-built in the side walls of the cover; and a nozzle tip with an internal and/or outer diameter no more than 1.2 mm.

Figure 9:
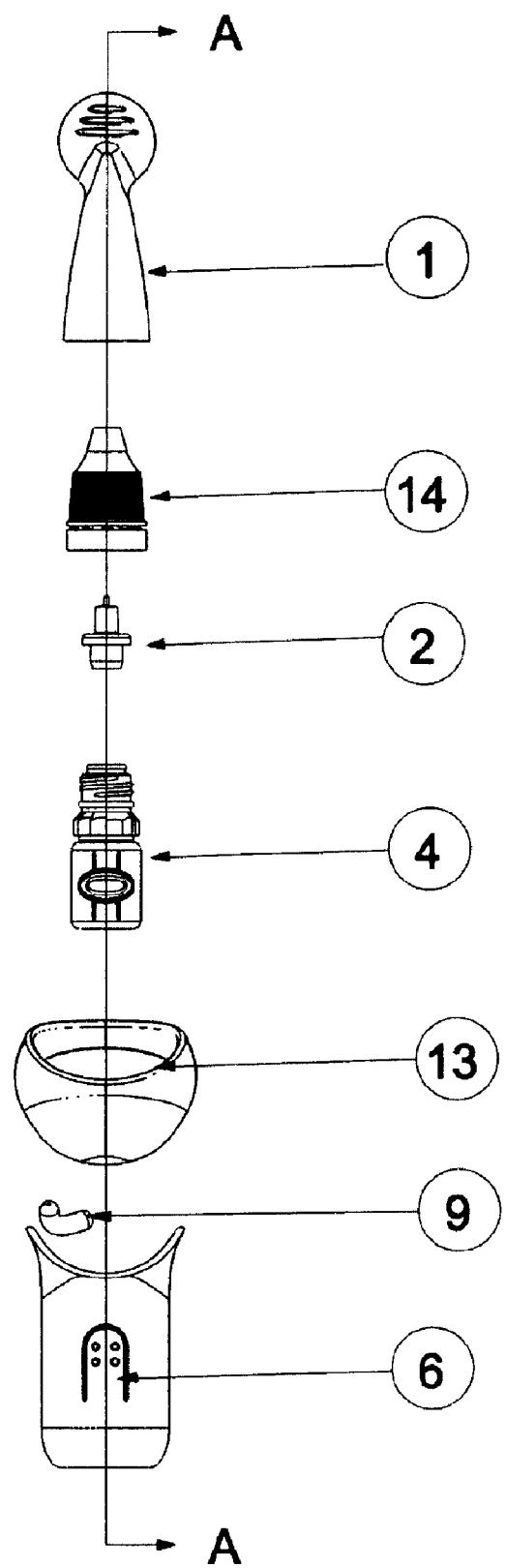
Figure 10:
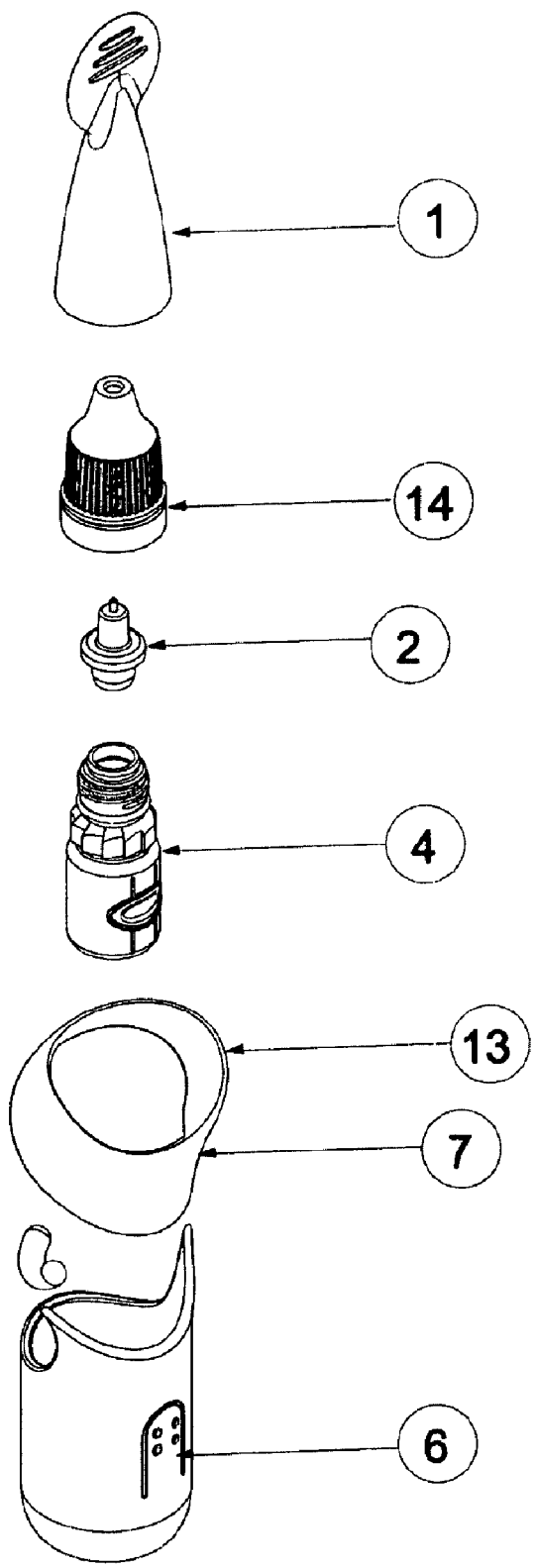

In this embodiment, the metered drop bottle comprises an external cap, a bottle cap, nozzle, eyedrop dispensing aid, an external cover and an orientation indicator as shown in Figures. The metered drop bottle of this embodiment delivers a single drop of microliter amounts of liquid from the nozzle. The complete assembly of the metered dose bottle of this embodiment is shown in FIGS. 9, 10 and 11.

Figure 8:
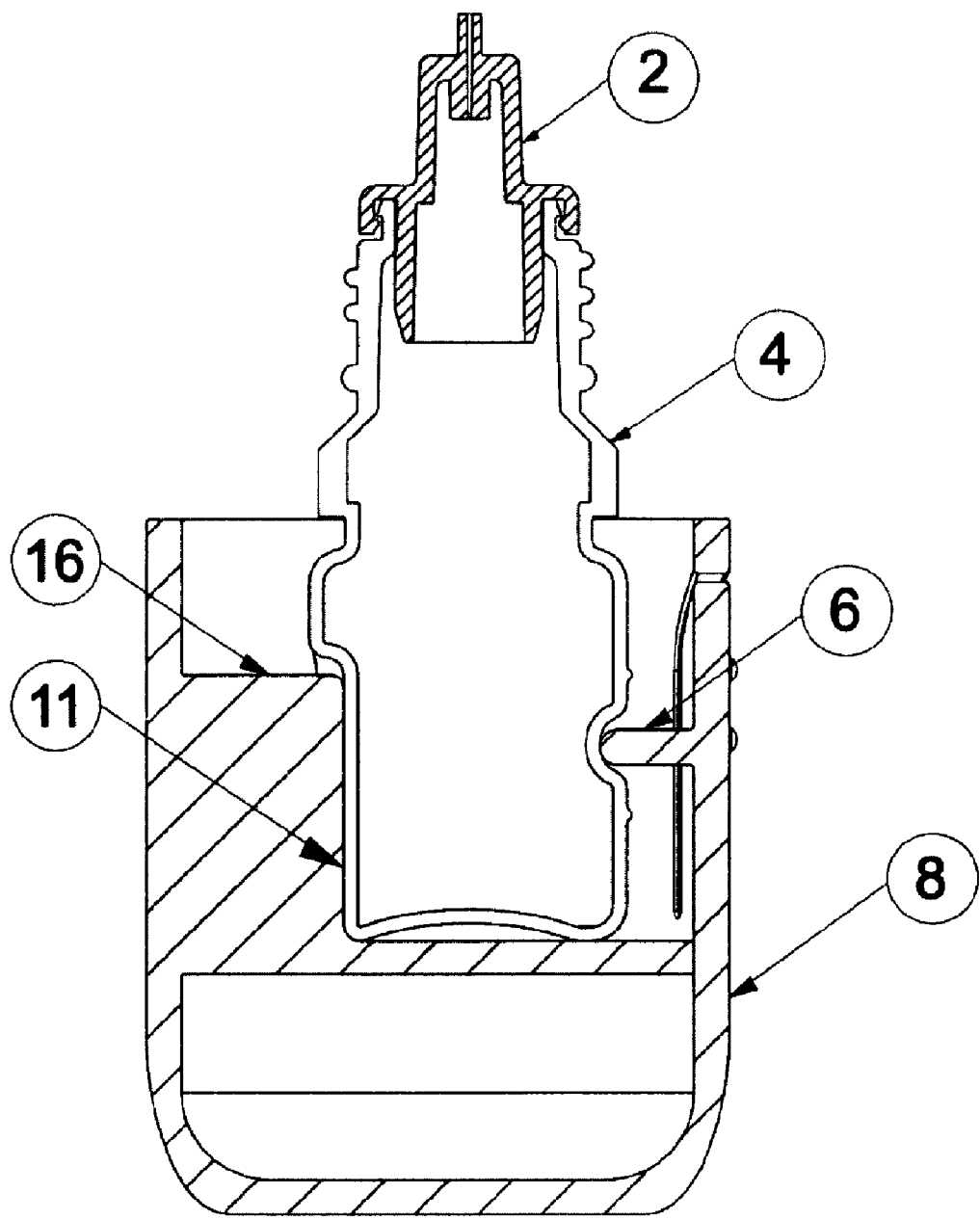

A bottle 4 used in this embodiment of the invention is shown in FIGS. 1 and 2. The bottle 4 of this embodiment is generally made up of a rigid material and has a flexible notch area 5 on its side wall. The notch can be of any geometry as long as it can be depressed by a plunger. The geometry of this notch has been calculated such that once a plunger 6 is inserted and pressed to its maximum depth, it would depress the flexible notch area of the bottle to decrease the internal volume of the bottle by a fixed amount and deliver a fixed volume of liquid to the nozzle.(FIG. 8). In a preferred embodiment, the flexible notch area is controllably depressed by the plunger by a distance of about 0.8 mm to about 2 mm in order to deliver a fixed volume of liquid from the bottle to the nozzle. In this case, the plunger is of a length suitable to depress the flexible notch area by a distance of about 0.8 mm to about 2 mm in order to deliver the fixed volume of liquid from the bottle to the nozzle. To dispense another drop, the user will have to make the bottle upright and again follow similar procedure. Ribs 15 have been provided on the bottle walls around the flexible notch area 5 to avoid flexing of any part of the peripheral walls other than the flexible notch area of the bottle, when the plunger is pressed. There is provided on the peripheral wall opposite to the flexible notch area, a slot 11 as shown in FIG. 1 and FIG. 8. This slot is used for matingly fitting a corresponding rib 16 on the external cover in order to correctly locate and place the bottle in the external cover and prevent its movement in the external cover (FIG. 8). In a preferred embodiment, the bottle is made transparent, so that opacifiers such as titanium dioxide and the like which might lead to incompatibility issues with medicaments need not be used. Also transparent bottles facilitate easier viewing of the amount of the fluid/medicament remaining in the bottle and also to check presence of particulate matter or turbidity in the fluid that might develop on storage of the medicament.

The nozzle 2 of the device of this embodiment of the invention is shown in FIGS. 3, 4, 5 and 6. The nozzle is designed such that it, in combination with the plunger and the flexible notch area of the bottle delivers a single drop of microliter amounts of the liquid to be dispensed. It is preferred that a drop of the liquid delivered has volume less than about 18 micro-liters. There is a step 3 provided to mate the broader portion of the nozzle to the narrower portion of the nozzle which leads to the dispensing end of the nozzle tip (FIG. 3). The nozzle tip of the bottle has an internal and/or outer diameter no more than 1.2 mm. The nozzle tip at its dispensing end has an internal diameter and an outer diameter and the tip is connected to an aperture inside the nozzle by a capillary tapering from the dispensing tip end to the aperture in the nozzle as can be seen in FIGS. 4, 5 and 6. FIG. 4 shows the cross section of a nozzle with the nozzle tip having an internal and external diameter, a platform width and an aperture. FIGS. 5 and 6 show cross section of the nozzles wherein the internal diameter of the nozzle tip is the same as the external diameter and there is no platform width. In an embodiment of the present invention, the aperture has an internal diameter of about 0.2 mm and the nozzle tip has an internal diameter of about 0.6 mm and an outer diameter of about 1.2 mm. In another embodiment, both the internal and outer diameter of the nozzle tip are the same, and may range from about 0.6 mm to about 1.2 mm. The nozzle functions to produce and dispense microliter sized drop of the liquid to be dispensed.

An external cover 8 surrounding the bottle is present in the embodiment of device of the invention and is shown in detail in FIGS. 7 and 8. The external cover is generally made of a rigid material and houses the plunger 6 for depressing the flexible notch area 5 of the bottle in order to deliver a fixed volume of liquid to the nozzle. In an embodiment of the device of the invention, a rib 16 is provided on the opposite side of the plunger in the external cover to matingly fit the slot 11 in the bottle. The rib of the external cover and the slot in the bottle are useful to locate and align the bottle precisely in the external cover 8 and lock the bottle in place avoid un-required movement of the bottle 4 in the cover. Different designs of the external cover with different locations of the plunger and the rib are possible. The external cover serves to house the plunger 6; serves as a base to the eyedrop dispensing aid 7 and the orientation indicator 9; provides a larger surface area for putting the label of contents of the medication and instructions for use; and helps to grip and hold the bottle 4 at an appropriate angle such that there is effective dispensing of the drop. In a preferred embodiment of the invention, the external cover is opaque to protect the medicament in the bottle from unwanted UV radiation exposure.

The external cap 1 of the bottle 4 as seen in FIGS. 9, 10 and 11, is placed on top of a bottle cap 14 and is designed in such a way that it is easy for the user to remove the cap. The external cap 1 may be fitted on to the bottle cap 14 or both the caps may be joined together by means known in the art, such as for example by heat sealing or by welding together or the like. Alternatively a single cap that covers the nozzle is used. The cap(s) primarily functions to protect the nozzle and the bottle contents from exposure to the outside environment. Another function of the cap(s) of the invention is to facilitate breaking of the seal of the bottle by generating a torque by the twisting action of the cap before the first administration of the medicament in order to make the bottle ready for subsequent use by the user. The shape of the external cap 1 as shown in FIGS. 9, 10 and 11 provides an ergonomic grip of the cap making the task of twisting the cap to generate a torque sufficient to break the seal of the bottle and also the removal of the cap before each administration of the medicament, much easier.

The metered drop bottle of the embodiment has an orientation indicator 9 as shown in FIG. 9, fitted onto the external cover 8. The orientation indicator of this embodiment contains a ball that locates itself on the crest of the indicator. The orientation indicator indicates to the patient whether the orientation of the bottle in relation to the eye is correct for proper dispensation of a desired sized drop into the eye. A particularly preferred example of a visual orientation indicator is a LED (Light emitting diode) display. The LED display can be used in such a way that when a proper orientation of the bottle is reached, a glowing light will give the patient a positive feedback about the proper orientation of the bottle during dispensing the medication. A sound signal may also be added in addition to the visual signal, to convey correct orientation of the bottle and the placement of the nozzle at the correct angle to the user. Alternatively various other orientation indicators which give visual feedback may be used or indicators which give an auditory signal or a combination of visual and auditory feedback indicators may be used in order to indicate to the patient the proper positioning and orientation of the bottle during administration of the medicament.

The metered drop bottle contains an eyedrop dispensing aid 7 in order to avoid touching the nozzle of the bottle to the surface of the eye and also to increase compliance in the applicator/patient by doing away with the fear of touching the nozzle to the eye. The eyedrop dispensing aid 7 used may be of a design known in the art. In an embodiment shown in FIGS. 9, 10 and 11, the eyedrop dispensing aid 7 is a hollow cup located on the top of the external cover 8, surrounding the area of the nozzle and the cap. The curvature of the top part 13 of the eyedrop dispensing aid is designed such that it fits well into the area surrounding the eye. In another embodiment, the eyedrop dispensing aid 7 may have a hollow ring located on the top of the external cover, surrounding the area of the nozzle and the cap. The eyedrop dispensing aid is designed such that the tip of the nozzle can be seen by a third person administering the medicament to the patient. The eyedrop dispensing aid may be made from a special soft feel material for a comfortable feel to the user.

In use, the user will twist the cap in order to break the seal of the bottle. Once the seal is broken, the cap is removed by the user. The lower eyelid of the eye in which the medicament is to be dispensed is pulled down slightly and the bottle is placed with the eyedrop dispensing aid surrounding the eye. Then the head is tilted back till the orientation indicator gives a positive feedback about the proper positioning of the bottle. In an embodiment, the red ball coming in the middle of the orientation indicator points to the right inclination while in an alternative embodiment, the glowing of the LED display gives an indication of the proper positioning of the bottle. The plunger is then pressed by the user to deliver a single drop of the liquid of microliter amounts from the nozzle into the eye. To dispense another drop, the bottle has to restored to the upright position and the same procedure followed again.

Embodiment 2: A metered bottle with a flexible notch area; an external cover surrounding the bottle; a plunger which is separate from the external cover and fitted into the external cover before use and a nozzle tip with an internal and/or outer diameter no more than 1.2 mm.

In this embodiment the metered bottle comprises a protective cap, bottle cap, nozzle, an external cover and a plunger which is separate from the external cover, as shown in FIG. 12. The metered bottle of this embodiment delivers a single drop of microliter amount from the delivery orifice of the nozzle.

The metered bottle of this embodiment has the cap(s) 14, bottle 4 and nozzle 2 similar to ones described in the embodiment I and also has an additional protective cap 19 for preventing the accidental pressing of the plunger. It may also contain the eyedrop dispensing aid 7 and the orientation indicator 9 as described in the embodiment 1, if it is to be used for delivering medicaments to the eye. However it differs from the device of the embodiment 1 in that it has a plunger 6 which is separate from the external cover 8 and fitted into the external cover before use. An example of the device of this embodiment is illustrated in FIG. 12.

An external cover 8 surrounding the bottle is present in the embodiment of device of the invention and is generally made of a rigid material and has a rectangular slot 18 for fitting the plunger 9. A rib is provided in the walls of external cover on the opposite side of the slot 18 to matingly fit the slot in the bottle. The rib of the external cover and the slot in the bottle are useful to locate and align the bottle precisely in the external cover 8 and lock the bottle in place so as to avoid unrequired movement of the bottle 4 in the cover.

The plunger 6 in this embodiment is generally rectangular to avoid rotation of the plunger when it has been fitted in the external cover. The plunger is designed to snap fit in a unidirectional way in the slot of the external cover. The plunger when pressed by the user during dispensing the medicament, depresses the flexible notch area 5 on the bottle and delivers a fixed volume of the liquid to the nozzle.

In use, the bottle is placed inside the cover such that the rib in the cover matingly fits the slot in the bottle. The plunger is then snap fitted in the slot provided in the cover for fitting the plunger. The lower eyelid of the eye in which the medicament is to be dispensed is pulled down slightly and the bottle is placed at a proper inclination to the tilted head. The plunger is then pressed by the user to deliver a drop of microliter amount of the medicament from the nozzle into the eye. To dispense another drop, the bottle has to be up righted and the same procedure is followed again.

The metered drop bottle and its various components used in the device of the invention can be made of any suitable material known in the art. Generally they are made from any mouldable or formed plastic. Typically the bottle may be made from Low Density Polyethylene (LDPE), Linear Low Density Polyethylene (LLDPE), High Density Polyethylene (HDPE) and the like or a combination thereof. Typically the nozzle may be made of Low Density Polyethylene (LDPE), Linear Low Density Polyethylene (LLDPE), High Density Polyethylene (HDPE) and the like or a combination thereof. Alternatively the nozzle may be made of a hydrophobic material or may be coated with a hydrophobic material such as a fluoropolymer like Teflon (polytetrafluoroethylene) and the like. Typically the cap(s) may be made from High Density Polyethylene (HDPE), Polypropylene (PP) and the like or combinations thereof. Typically the dispensing aid may be made from Polypropylene (PP), Linear Low Density Polyethylene (LLDPE), Low Density Polyethylene (LDPE), Thermoplastic Elastomer (TPE), Acrylonitrile Butadiene Styrene (ABS), Styrene Acrylonitrile (SAN) and the like or a combination thereof. Typically the orientation indicator may be made from High Density Polyethylene (HDPE), Low Density Polyethylene (LDPE), Linear Low Density Polyethylene (LLDPE) and the like or combinations thereof.

Typically the bottle may be made by the process of injection blow moulding. Injection blow moulding involves two processes: Injection moulding and blow moulding. In injection moulding, the molten polymer is fed into a manifold where it is injected through nozzles into a hollow, heated preform mould. The preform mould forms the external shape and is clamped around a mandrel (the core rod) which forms the internal shape of the preform. The preform consists of a fully formed bottle/jar neck with a thick tube of polymer attached, which will form the body. In blow moulding, the preform is placed into chilled blow mould and a core rod is rotated and clamped into the hollow, chilled blow mould. The core rod opens and allows compressed air into the preform, which inflates it to the finished article shape, defined by the blow mould. The rest of the components of the metered dose bottle may be made by injection moulding. Injection molding is a technique in which the molten plastic is injected at high pressure and temperature into a closed mould, which has the inverse of the product's shape, thereby when the mould is cooled and opened, the required product can be got.

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention. Accordingly, it is to be understood that the drawings and descriptions herein are proffered by way of example to facilitate comprehension of the invention and should not be construed to limit the scope thereof.

We claim:

1. A metered drop bottle for dispensing microliter amounts of a liquid in the form of a drop comprising:
   (a) a bottle body having walls defining an internal volume, wherein the walls comprise a bottom wall and side walls, wherein the side walls comprise a flexible portion to decrease the internal volume by a fixed volume, wherein the flexible portion is a flexible notch;
   (b) a plunger with a fixed stroke between a minimum depth position and a maximum depth position for depressing the flexible notch;
   (c) a nozzle tip formed around an opening, said nozzle tip having an internal and/or outer diameter in a range of from 0.6 mm to 1.2 mm; and
   (d) an external cover which surrounds the bottle body and houses the plunger,
   wherein the flexible notch area is controllably depressed by the plunger by a distance of about 0.8 mm to about 2 mm in order to deliver a predetermined volume of liquid from the bottle to the opening of the nozzle tip.

2. A metered drop bottle as in claim 1, wherein the bottle dispenses a drop of predetermined size of about 14 microliter to about 25 microliter of the liquid to be dispensed.

3. A metered drop bottle as in claim 2, wherein the bottle dispenses a drop of predetermined size of about 14 microliter to about 18 microliter of the liquid to be dispensed.

4. A metered drop bottle as in claim 1, wherein the plunger is in-built in the sidewalls of the external cover.

5. A metered drop bottle as in claim 1, wherein the plunger is separate from the external cover and is fitted into the external cover before use.

6. A metered drop bottle as in claim 1, wherein the bottle further comprises at least one cap.

7. A metered drop bottle as in claim 1, wherein the bottle body comprises ribs around the flexible notch area.

8. A metered drop bottle as in claim 1, wherein the bottle body further comprises a slot.

9. A metered drop bottle as in claim 8, wherein the external cover comprises a rib for fitting into the slot of the bottle body.

10. A metered drop bottle as in claim 1, wherein the external cover is opaque.

11. A metered drop bottle as in claim 1, wherein the bottle body is transparent.

12. A metered drop bottle as in claim 1, wherein the bottle further comprises an orientation indicator.

13. A metered drop bottle as in claim 1, wherein the bottle is used for administration of medicament to the eye of a user in need of the medicament.

14. A metered drop bottle as in claim 13, wherein the bottle further comprises an eyedrop dispensing aid.

15. A metered drop bottle as in claim 1, wherein the plunger is fitted in a sidewall of the external cover, the external cover being rigid.

* * * * *